US012490999B2

(12) United States Patent
Shelton, IV et al.

(10) Patent No.: US 12,490,999 B2
(45) Date of Patent: Dec. 9, 2025

(54) SURGICAL SYSTEM AND METHODS OF ASSEMBLY AND DISASSEMBLY OF SURGICAL INSTRUMENT

(71) Applicant: Cilag GmbH International, Zug (CH)

(72) Inventors: Frederick E. Shelton, IV, Hillsboro, OH (US); Jacqueline C. Aronhalt, Loveland, OH (US); Shane R. Adams, Lebanon, OH (US); Taylor W. Aronhalt, Loveland, OH (US); Cameron D. McLain, Deer Park, OH (US)

(73) Assignee: Cilag GmbH International, Zug (CH)

( * ) Notice: Subject to any disclaimer, the term of this patent is extended or adjusted under 35 U.S.C. 154(b) by 522 days.

(21) Appl. No.: 17/854,641

(22) Filed: Jun. 30, 2022

(65) Prior Publication Data

US 2024/0000476 A1 Jan. 4, 2024

(51) Int. Cl.
*A61B 17/32* (2006.01)
*A61B 17/00* (2006.01)

(52) U.S. Cl.
CPC ................. *A61B 17/320092* (2013.01); *A61B 2017/0046* (2013.01); *A61B 2017/00477* (2013.01); *A61B 2017/320094* (2017.08)

(58) Field of Classification Search
CPC .... A61B 17/320092; A61B 17/320094; A61B 2017/0046; A61B 2017/00477; A61B 18/1442; A61B 18/1445
See application file for complete search history.

(56) References Cited

U.S. PATENT DOCUMENTS

| | | | | |
|---|---|---|---|---|
| 384,592 | A * | 6/1888 | Ross | B25B 13/48 7/165 |
| 5,014,379 | A | 5/1991 | Hull et al. | |
| 5,057,119 | A | 10/1991 | Clark et al. | |
| 7,316,424 | B2 | 1/2008 | Kardeis et al. | |
| 7,354,440 | B2 | 4/2008 | Truckai et al. | |
| 7,381,209 | B2 | 6/2008 | Truckai et al. | |
| 8,061,014 | B2 | 11/2011 | Smith et al. | |
| 8,485,075 | B1 * | 7/2013 | Gauthier | A61B 17/8875 81/479 |
| 8,663,220 | B2 | 3/2014 | Wiener et al. | |

(Continued)

FOREIGN PATENT DOCUMENTS

| | | |
|---|---|---|
| CN | 111920164 A | 11/2020 |
| EP | 3505076 A2 | 7/2019 |

OTHER PUBLICATIONS

U.S. Appl. No. 17/854,050; and.

(Continued)

*Primary Examiner* — Kathleen S Holwerda
(74) *Attorney, Agent, or Firm* — FROST BROWN TODD LLP

(57) ABSTRACT

A surgical kit and related methods of assembly and disassembly include a surgical instrument having an end effector, a shaft assembly, and a body assembly. The surgical instrument includes a predetermined access portion configured to be at least partially removed for accessing an interior therein. The surgical kit also includes an instrument tool assembly with a tool body, a torque wrench connected to the tool body, and a removal portion for gaining access to the interior of the surgical instrument.

19 Claims, 7 Drawing Sheets

(56) References Cited

U.S. PATENT DOCUMENTS

| | | | |
|---|---|---|---|
| 8,820,605 B2 | 9/2014 | Shelton, IV | |
| 9,125,662 B2 | 9/2015 | Shelton, IV | |
| 9,314,308 B2 | 4/2016 | Parihar et al. | |
| 9,421,060 B2 | 8/2016 | Monson et al. | |
| 9,872,696 B2 | 1/2018 | Smith et al. | |
| 9,949,785 B2 | 4/2018 | Price et al. | |
| 10,426,508 B2 | 10/2019 | Smith et al. | |
| 10,624,709 B2 | 4/2020 | Remm | |
| 10,660,695 B2 | 5/2020 | Madan et al. | |
| 10,835,307 B2 | 11/2020 | Shelton, IV et al. | |
| 10,892,995 B2 | 1/2021 | Shelton, IV et al. | |
| 11,229,471 B2 | 1/2022 | Shelton, IV et al. | |
| 11,229,472 B2 | 1/2022 | Shelton, IV et al. | |
| 11,259,830 B2 | 3/2022 | Nott et al. | |
| 11,291,495 B2 | 4/2022 | Yates et al. | |
| 11,364,075 B2 | 6/2022 | Yates et al. | |
| 11,419,667 B2 | 8/2022 | Messerly et al. | |
| 11,589,888 B2 | 2/2023 | Shelton, IV et al. | |
| 11,690,642 B2 | 7/2023 | Black et al. | |
| 2006/0079874 A1 | 4/2006 | Faller et al. | |
| 2007/0191713 A1 | 8/2007 | Eichmann et al. | |
| 2008/0200940 A1 | 8/2008 | Eichmann et al. | |
| 2009/0171147 A1 | 7/2009 | Lee et al. | |
| 2012/0116380 A1* | 5/2012 | Madan | H01M 10/46 606/1 |
| 2012/0292367 A1 | 11/2012 | Morgan et al. | |
| 2017/0105753 A1* | 4/2017 | Conlon | B25B 27/02 |
| 2021/0346086 A1 | 11/2021 | Hase | |
| 2024/0000474 A1 | 1/2024 | Shelton, IV et al. | |
| 2024/0000475 A1 | 1/2024 | Shelton, IV et al. | |
| 2024/0000491 A1 | 1/2024 | Shelton, IV et al. | |
| 2024/0000526 A1 | 1/2024 | Shelton, IV et al. | |
| 2024/0001416 A1 | 1/2024 | Shelton, IV et al. | |
| 2024/0003820 A1 | 1/2024 | Shelton, IV et al. | |
| 2024/0006048 A1 | 1/2024 | Shelton, IV et al. | |
| 2024/0006810 A1 | 1/2024 | Carranza et al. | |

OTHER PUBLICATIONS

U.S. Appl. No. 17/854,166.

Anonymous: "pcb design—Detachable "debug" portion of PCB?—Electrical Engineering Stack Exchange," downloaded from https://electronics.stackexchange.com/questions/356423/detachable-debug-portion-of-pcb, retrieved on Nov. 22, 2023, XP093104291, 4 pgs.

International Search Report and Written Opinion dated Sep. 8, 2023 for Application No. PCT/IB2023/056598, 13 pgs.

International Search Report and Written Opinion dated Oct. 10, 2023 for Application No. PCT/IB2023/056599, 12 pgs.

International Search Report and Written Opinion dated Dec. 18, 2023 for Application No. PCT/IB2023/056602, 21 pgs.

U.S. Appl. No. 62/611,339, filed Dec. 28, 2017, by Shelton, IV et al., entitled "Robot Assisted Surgical Platform."

U.S. Appl. No. 62/611,340, filed Dec. 28, 2017, by Shelton, IV et al., entitled "Cloud-Based Medical Analytics."

U.S. Appl. No. 62/611,341, filed Dec. 28, 2017, by Shelton, IV et al., entitled "Interactive Surgical Platform."

* cited by examiner

SURGICAL SYSTEM AND METHODS OF ASSEMBLY AND DISASSEMBLY OF SURGICAL INSTRUMENT

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; U.S. Pat. No. 8,663,220, entitled "Ultrasonic Electrosurgical Instruments," issued Mar. 4, 2014, the disclosure of which is incorporated by reference herein, in its entirety; U.S. Pat. No. 10,835,307, entitled "Modular Battery Powered Handheld Surgical Instrument Containing Elongated Multi-Layered Shaft," issued Nov. 17, 2020, the disclosure of which is incorporated by reference herein, in its entirety; and U.S. Pat. No. 11,229,471, entitled "Modular Battery Powered Handheld Surgical Instrument with Selective Application of Energy Based on Tissue Characterization," issued Jan. 25, 2022, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on May 2, 2019, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023, the disclosure of which is incorporated by reference herein, in its entirety.

Such instruments and robotic surgical systems may be further be incorporated into a surgical system for performing procedures in a surgical environment, such as surgical operating theaters or rooms in a healthcare facility. A sterile field is typically created around the patient and may include properly attired, scrubbed healthcare professions as well as desired furniture and/or fixtures. Examples of such surgical systems and associated features are disclosed in U.S. Pat. Pub. No. 2019/0201046, entitled "Method for Controlling Smart Energy Devices," published on Jul. 4, 2019, issued as U.S. Pat. No. 11,589,888 on Feb. 28, 2023, the disclosure of which is incorporated by reference herein, in its entirety; U.S. Pat. Pub. No. 2019/0201080, entitled "Ultrasonic Energy Device Which Varies Pressure Applied by Clamp Arm to Provide Threshold Control Pressure at a Cut Progression Location," published on Jul. 4, 2019, issued as U.S. Pat. No. 11,419,667 on Aug. 23, 2022, the disclosure of which is incorporated by reference herein, in its entirety; U.S. Pat. Pub. No. 2019/0201091, entitled "Radio Frequency Energy Device for Delivering Combined Electrical Signals," published Jul. 4, 2019, issued as U.S. Pat. No. 11,364,075 on Jun. 21, 2022, the disclosure of which is incorporated by reference herein, in its entirety; U.S. Pat. Pub. No. 2019/0274717, entitled "Methods for Controlling Temperature in Ultrasonic Device," published Sep. 12, 2019, issued as U.S. Pat. No. 11,259,830 on Mar. 1, 2022, the disclosure of which is incorporated by reference herein, in its entirety; and U.S. Pat. Pub. No. 2019/0207857, entitled "Surgical Network Determination of Prioritization of Communication, Interaction, or Processing Based on System or Device Needs," published Jul. 4, 2019, issued as U.S. Pat. No. 10,892,995 on Jan. 12, 2021, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
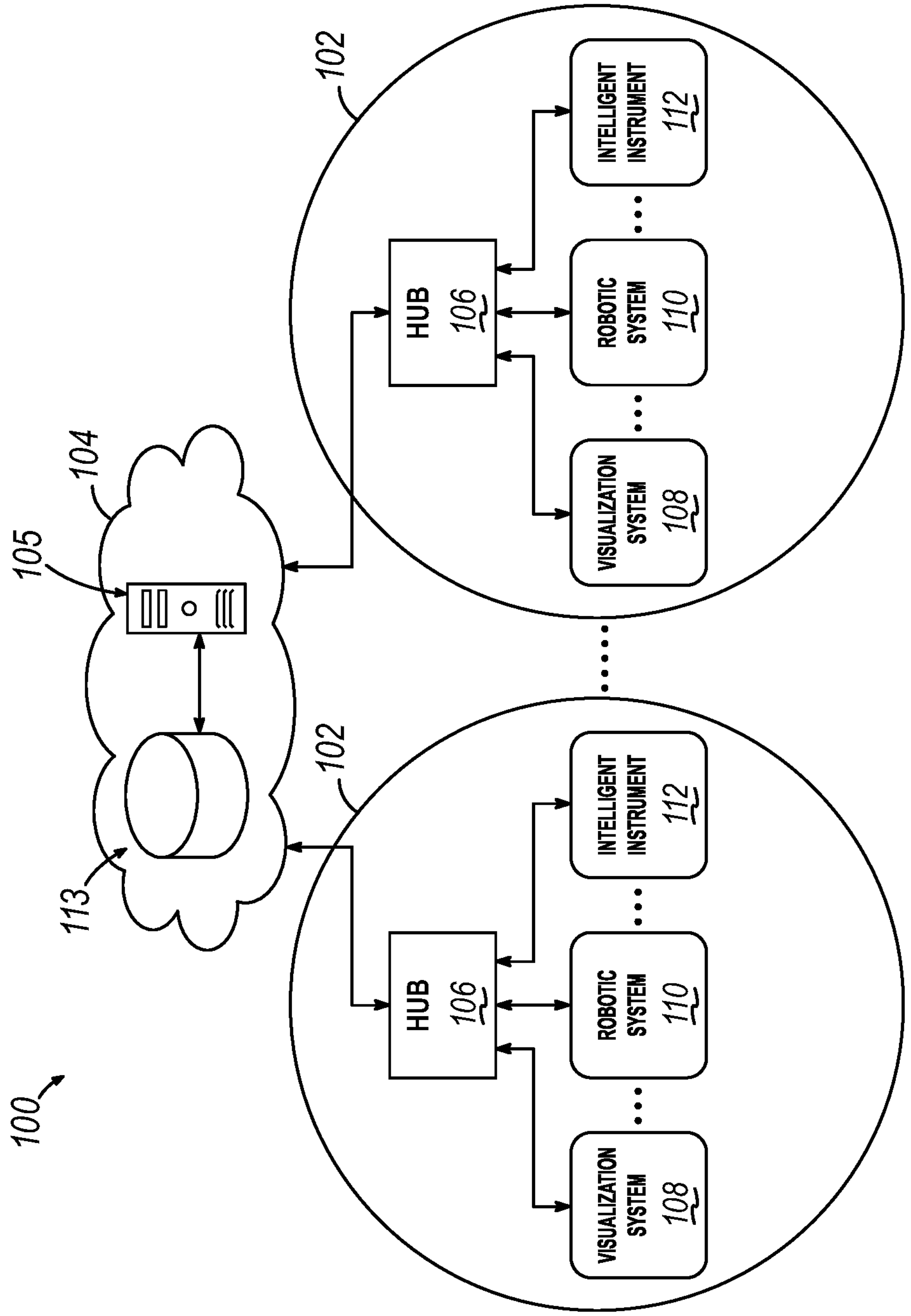
FIG. 1 depicts a block diagram of an example a computer-implemented interactive surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. EXAMPLE OF A SURGICAL SYSTEM

With respect to FIG. 1, a computer-implemented interactive surgical system (100) includes one or more surgical systems (102) and a cloud-based system (e.g., a cloud (104) that may include a remote server (113) coupled to a storage device (105)). Each surgical system (102) of the present example includes at least one surgical hub (106) in communication with cloud (104) that may include a remote server (113). In one example, as illustrated in FIG. 1, surgical system (102) includes a visualization system (108), a robotic system (110), and a handheld intelligent surgical instrument (112), which are configured to communicate with one another and/or hub (106). In some aspects, a surgical system (102) may include an M number of hubs (106), an N number of visualization systems (108), an O number of robotic systems (110), and a P number of handheld intelligent surgical instruments (112), where M, N, O, and P are integers greater than or equal to one. In any case, any suitable combination of features provided below may be incorporated into an exemplary surgical system, such as surgical system (100), and used in the surgical theater in order to perform a desired surgical procedure as would be apparent to one skilled in the art in view of the teachings herein.

Figure 2:
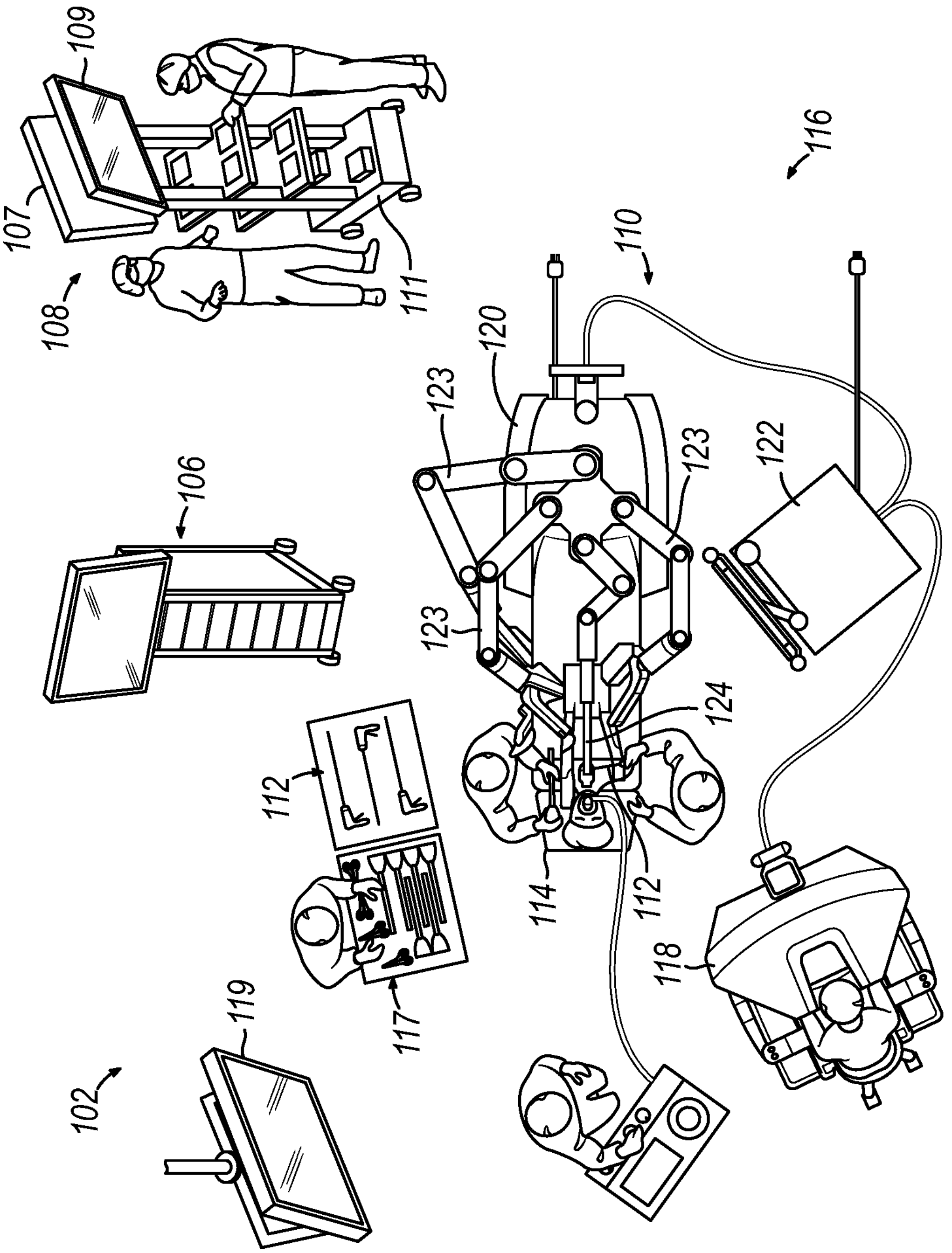
FIG. 2 depicts a top schematic view of an example of a surgical system for performing a surgical procedure in an operating room of a healthcare facility.

FIG. 2 depicts an example of a surgical system (102) being used to perform a surgical procedure on a patient who is lying down on an operating table (114) in a surgical operating room (116). A robotic system (110) is used in the surgical procedure as a part of surgical system (102). Robotic system (110) includes a surgeon's console (118), a patient side cart (120) (surgical robot), and a surgical robotic hub (122). Patient side cart (120) can manipulate at least one removably coupled surgical tool (117) with any one of a plurality of surgical arms (123) through a minimally invasive incision in the body of the patient while the surgeon views the surgical site through console (118). An image of the surgical site can be obtained by a medical imaging device (124), which can be manipulated by patient side cart (120) to orient imaging device (124). Robotic hub (122) can be used to process the images of the surgical site for subsequent display to the surgeon through console (118).

Other types of robotic systems can be readily adapted for use with surgical system (102). Various examples of robotic systems and surgical tools that are suitable for use with the present disclosure are described in U.S. Provisional Patent Application Ser. No. 62/611,339, entitled "Robot Assisted Surgical Platform," filed Dec. 28, 2017, the disclosure of which is herein incorporated by reference in its entirety.

Various examples of cloud-based analytics that are performed by cloud (104, and are suitable for use with the present disclosure, are described in U.S. Provisional Patent Application Ser. No. 62/611,340, entitled Cloud-Based Medical Analytics," filed Dec. 28, 2017, the disclosure of which is herein incorporated by reference in its entirety.

In various aspects, imaging device (124) includes at least one image sensor and one or more optical components. Suitable image sensors include, but are not limited to, Charge-Coupled Device (CCD) sensors and Complementary Metal-Oxide Semiconductor (CMOS) sensors. In various aspects, imaging device (124) is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. Some aspects of spectral and multi-spectral imaging are described in greater detail under the heading "Advanced Imaging Acquisition Module" in U.S. Provisional Patent Application Ser. No. 62/611,341, entitled "Interactive Surgical Platform," filed Dec. 28, 2017, the disclosure of which is herein incorporated by reference in its entirety.

Strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In addition to the introduction of any features of surgical system (100), furniture, or fixtures into the sterile field requiring sterilization, additional complications may result from removal of these features from the sterile field, particularly when such features may have contacted, or presumed to have contacted, the patient, including any tissues and/or fluids associated with the surgical procedure. Such contamination of these features from the patient often requires special consideration during or after the surgical procedure, particularly when processing these features for disposal, reuse, or remanufacturing as desired. In one example, surgical system (100) and/or healthcare professionals associated with the surgical procedure may be specifically equipped to address such processing as discussed below in greater detail.

As illustrated in FIG. 2, a primary display (119) is positioned in the sterile field to be visible to an operator at operating table (114). In addition, a visualization tower (111) is positioned outside the sterile field. Visualization tower (111) includes a first non-sterile display (107) and a second non-sterile display (109), which face away from each other. Visualization system (108), guided by hub (106), is configured to utilize displays (107, 109, 119) to coordinate information flow to operators inside and outside the sterile field. For example, hub (106) may cause visualization system (108) to display a snapshot of a surgical site, as recorded by imaging device (124), on a non-sterile display (107) or (109), while maintaining a live feed of the surgical site on the primary display (119). The snapshot on non-sterile display (107) or display (109) can permit a non-sterile operator to perform a diagnostic step relevant to the surgical procedure, for example.

In one aspect, hub (106) is also configured to route a diagnostic input or feedback entered by a non-sterile operator at visualization tower (111) to primary display (119) within the sterile field, where it can be viewed by a sterile operator at the operating table. In one example, the input can be in the form of a modification to the snapshot displayed on non-sterile display (107) or display (109), which can be routed to primary display (119) by hub (106).

Referring to FIG. 2, a surgical instrument (112) is being used in the surgical procedure as part of surgical system (102). Hub (106) is also configured to coordinate information flow to a display of the surgical instrument (112) such as in, for example, U.S. Provisional Patent Application Ser. No. 62/611,341, entitled "Interactive Surgical Platform," filed Dec. 28, 2017, the disclosure of which is herein incorporated by reference in its entirety. A diagnostic input or feedback entered by a non-sterile operator at visualization tower (111) can be routed by hub (106) to surgical instrument display (115) within the sterile field, where it can be viewed by the operator of surgical instrument (112). Example surgical instruments that are suitable for use with surgical system (102) are described under the heading "Surgical Instrument Hardware" and in U.S. Provisional Patent Application Ser. No. 62/611,341, entitled "Interactive Surgical Platform," filed Dec. 28, 2017, the disclosure of which is herein incorporated by reference in its entirety, for example.

Figure 3:
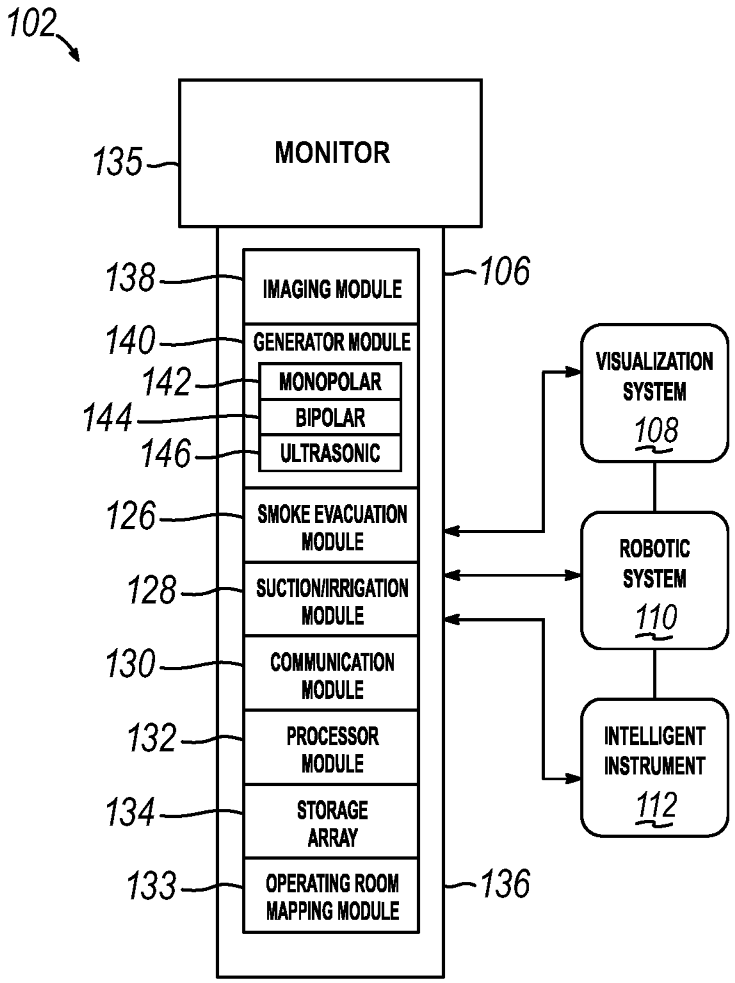
FIG. 3 depicts a side schematic view of an example of a surgical hub of the surgical system of FIG. 2.

Referring now to FIG. 3, a hub (106) is depicted in communication with a visualization system (108), a robotic system (110), and a handheld intelligent surgical instrument (112). Hub (106) includes a hub display (135), an imaging module (138), a generator module (140), a communication module (130), a processor module (132), and a storage array (134). In certain aspects, as illustrated in FIG. 3, hub (106) further includes a smoke evacuation module (126), a suction/irrigation module (128), and/or an operating room mapping module (133).

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure (136) offers a unified environment for managing the power, data, and fluid lines, which reduces the frequency of entanglement between such lines.

Figure 4:
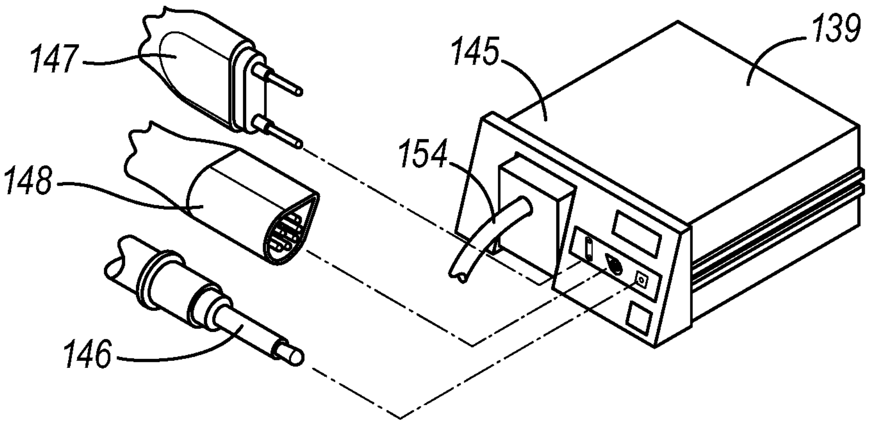
FIG. 4 depicts a perspective view of a combination generator module with bipolar, ultrasonic, and monopolar contacts of the surgical system of FIG. 2.

Referring to FIGS. 3-4, aspects of the present disclosure are presented for a hub modular enclosure (136) that allows the modular integration of a generator module (140), a smoke evacuation module (126), and a suction/irrigation module (128). Hub modular enclosure (136) further facilitates interactive communication between modules (140, 126, 128). As shown in FIG. 4, generator module (140) can be a generator module with integrated monopolar, bipolar, and ultrasonic components supported in a single housing unit (139) slidably insertable into hub modular enclosure (136). As illustrated in FIG. 4, generator module (140) can be configured to connect to a monopolar device (146), a bipolar device (147), and an ultrasonic device (148). Alternatively, generator module (140) may comprise a series of monopolar, bipolar, and/or ultrasonic generator modules that interact through hub modular enclosure (136). Hub modular enclosure (136) can be configured to facilitate the insertion of multiple generators and interactive communication between the generators docked into the hub modular enclosure (136) so that the generators would act as a single generator.

Figure 5:
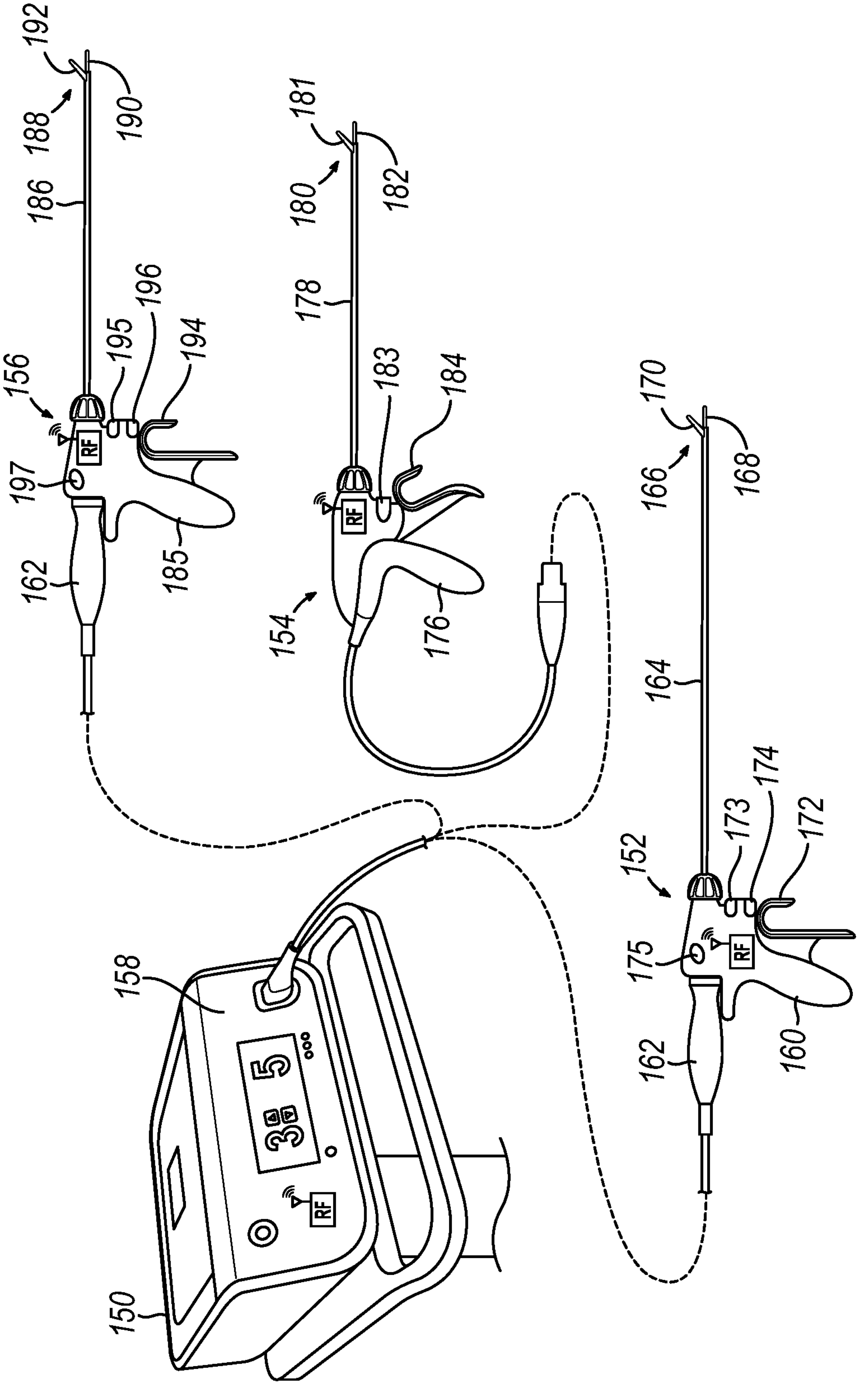
FIG. 5 depicts a side schematic view of an exemplary generator and various examples of surgical instruments for use with the surgical system of FIG. 2.

FIG. 5 illustrates one form of a generator (150) and various surgical instruments (152, 154, 156) usable therewith, where surgical instrument (152) is an ultrasonic surgical instrument (152), surgical instrument (154) is an RF electrosurgical instrument (154), and multifunction surgical instrument (156) is a combination ultrasonic/RF electrosurgical instrument (156). Generator (150) is configurable for use with a variety of surgical instruments. According to various forms, generator (150) may be configurable for use with different surgical instruments of different types including, for example, ultrasonic surgical instruments (152), RF electrosurgical instruments (154), and multifunction surgical instruments (156) that integrate RF and ultrasonic energies delivered simultaneously from generator (150). Although generator (150) of the present example in FIG. 5 is shown separate from surgical instruments (152, 154, 156), generator (150) may alternatively be formed integrally with any of surgical instruments (152, 154, 156) to form a unitary surgical system. Generator (150) comprises an input device (158) located on a front panel of generator (150) console. Input device (158) may comprise any suitable device that generates signals suitable for programming the operation of generator (150). Generator (150) may be configured for wired or wireless communication.

Generator (150) of the present example is configured to drive multiple surgical instruments (152, 154, 156). One example of such surgical instrument is ultrasonic surgical instrument (152) and comprises a handpiece (160), an ultrasonic transducer 162, a shaft assembly (164), and an end effector (166). End effector (166) includes an ultrasonic blade (168) acoustically coupled to ultrasonic transducer (162) and a clamp arm (170). Handpiece (160) has a trigger (172) to operate clamp arm (170) and a combination of toggle buttons (173, 174, 175) to energize and drive ultrasonic blade (168) or other function. Toggle buttons (173, 174, 175) can be configured to energize ultrasonic transducer (162) with generator (150).

Generator (150) also is configured to drive another example of surgical instrument (154). RF electrosurgical instrument (154) includes a handpiece (176), a shaft assembly (178), and an end effector (180). End effector (180) includes electrodes in clamp arms (181, 182) and return through an electrical conductor portion of shaft assembly (178). Electrodes are coupled to and energized by a bipolar energy source within generator (150). Handpiece (176) includes a trigger (183) to operate clamp arms (181, 182) and an energy button (184) to actuate an energy switch to energize electrodes in end effector (180).

Generator (150) also is configured to drive multifunction surgical instrument (156). Multifunction surgical instrument (156) includes a handpiece (185), a shaft assembly (186), and an end effector (188). End effector (188) has an ultrasonic blade (190) and a clamp arm (192). Ultrasonic blade (190) is acoustically coupled to ultrasonic transducer (162). Handpiece (185) has a trigger (194) to operate clamp arm (192) and a combination of toggle buttons (195, 196, 197) to energize and drive ultrasonic blade (190) or other function. Toggle buttons (195, 196, 197) can be configured to energize ultrasonic transducer (162) with generator (150) and energize ultrasonic blade (190) with a bipolar energy source also contained within generator (150). It will be appreciated that handpieces (160, 176, 185) may be replaced with a robotically controlled instrument for incorporating one or more aspects of surgical instruments (152, 154, 156). Accordingly, the term "handpiece" should not be limited to this context and to handheld use.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions, all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device. Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

II. SURGICAL SYSTEM AND METHODS OF ASSEMBLY AND DISASSEMBLY OF SURGICAL INSTRUMENT

Manufacturers of medical devices often offer a wide array of products tailored to fit the individual preferences of the surgeon, hospital, and patient. In order to address these preferences, manufacturers may distribute surgical kits of individual components that require assembly prior to use. In many cases, this assembly occurs immediately prior to use and can be performed by hand without tools. Such assembly may include connecting two electrical connections together or connecting a vacuum line to a vacuum canister. In other cases, this assembly may require specialized tools, such as a wrench to secure a nut.

As with assembly, it may be desirable to disassemble components after use. Disassembly may be advantageous for reasons such as reusing certain components, analyzing internal wear items, and recycling or refurbishing high value components. Disassembly may require use of certain tools and instruments which are specialized to access and remove these components without damaging them.

Surgical instruments, such as instruments (152, 154, 156) and other instruments shown and described herein, s often the most valuable component of surgical kits, but, in many cases, are one-time use components and thus not reusable. If any of such instruments (152, 154, 156) are reusable, these instruments (152, 154, 156) may require at least partial disassembly and cleaning after use to remove any biological material that may have attached to the instrument (152, 154, 156). Whether instrument (152, 154, 156) is one-time use or reusable, instrument (152, 154, 156) will often contain high value components, such as transducers, circuit boards, and sensors that can be either reused or recycled rather than be disposed of.

Accessing and harvesting these high value components can often be a laborious task and in many scenarios is cost prohibitive with little to no design consideration to component harvesting after use. For example, certain non-reversible assembly procedures may be used in the assembly of such instruments (152, 154, 156) to discourage them from being taken apart. These non-reversible procedures may include over-molding, use of adhesives, soldering, use of conformal coatings, one-time fittings, and non-reversible fasteners. Surgical kits, including instruments (152, 154, 156), may have one or more features configured to encourage harvesting of high value and recyclable components. Furthermore, instruments (152, 154, 156) may include the use of assembly practices such as reversible adhesives, standard fasteners, special access ports, and electrical connectors rather than solder joints.

Figure 6:
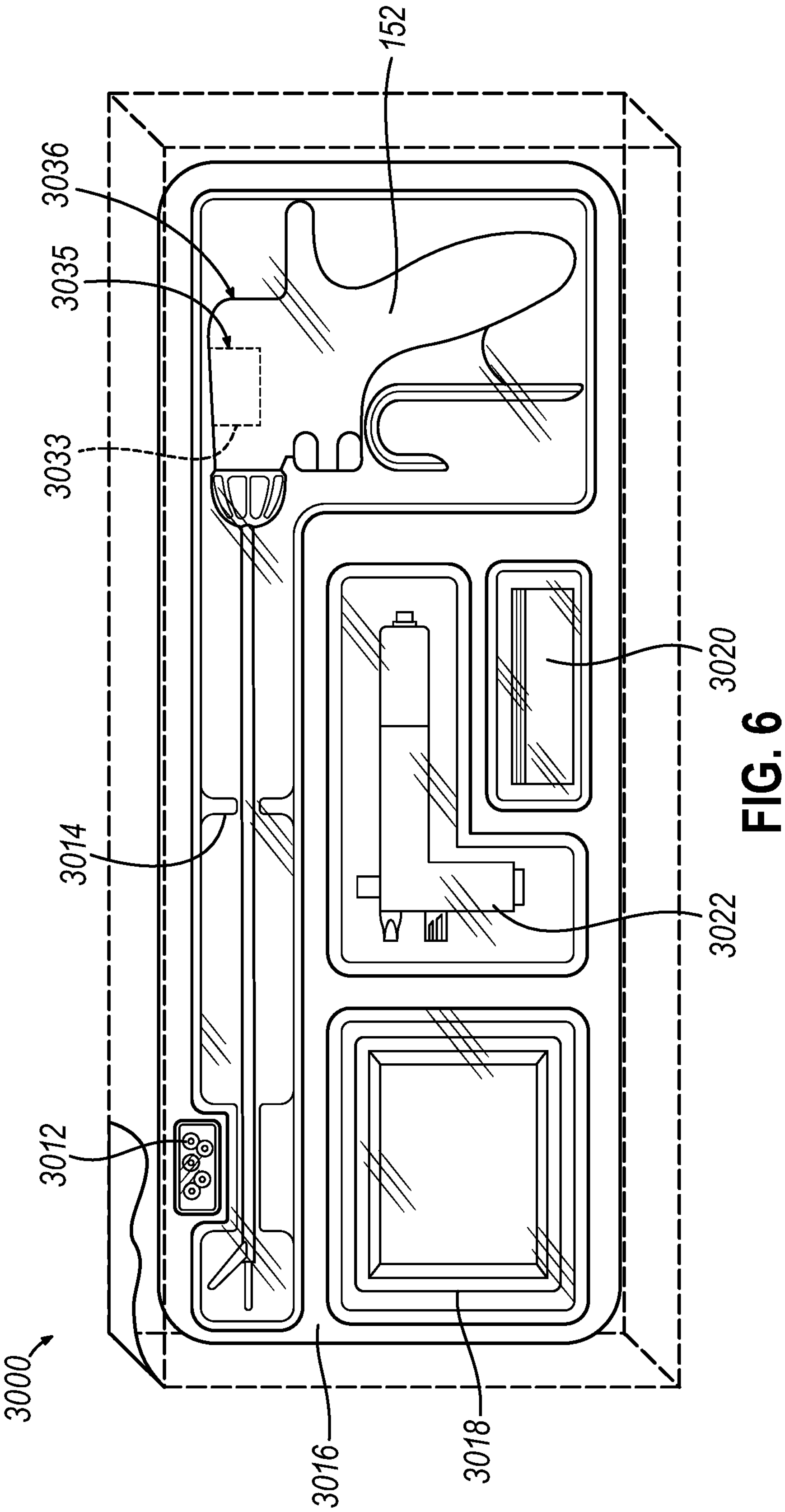
FIG. 6 depicts a front schematic view of a surgical kit including the surgical instrument of FIG. 5 and an example of an instrument tool assembly.

To this end, FIG. 6 depicts a surgical kit (3000) for use in a surgical setting with one or more such features configured to encourage harvesting of high value and recyclable components. Kit (3000) includes a tray (3016) designed to hold and present components and, in the present example, includes all of the items needed to perform a particular operation, although alternative examples may have more or less components as desired for all or part of a procedure. Such surgical kits (3000) can simplify ordering by using a single part number for the entire kit (3000) rather than ordering each component separately, which may result in inadvertently omitting a desired component for a surgical procedure. Surgical kit (3000) may be shipped sterile, can be sterilized on site, or can be used non-sterile if desired. Components in surgical kit (3000) of the present example include instrument (152), replacement parts (3012) for instrument (152), a parts compartment (3018) built into tray (3016) for capturing spare or discarded parts, a parts container (3020), such as a TYVEK® bag described herein, for capturing spare or discarded parts that may need to be fluidly sealed, an instrument tool assembly (3022), and instructions for use (not shown). While surgical kit (3000) incorporates instrument (152) therein, any surgical instrument, such instruments (154, 156) or other such instruments described herein, may be incorporated into an alternative kit such that the invention is not intended to be unnecessarily limited to instrument (152).

More particularly, instrument tool assembly (3022), which may also be referred to herein as tool (3022), is configured to act upon instrument (152) to gain access to the high value and recyclable components of instrument (152). In this case, tool (3022) is provided in kit (3000) along with instrument (1520 to ensure availability for use with instrument (152), such as upon disassembly of instrument (152).

Figure 7:
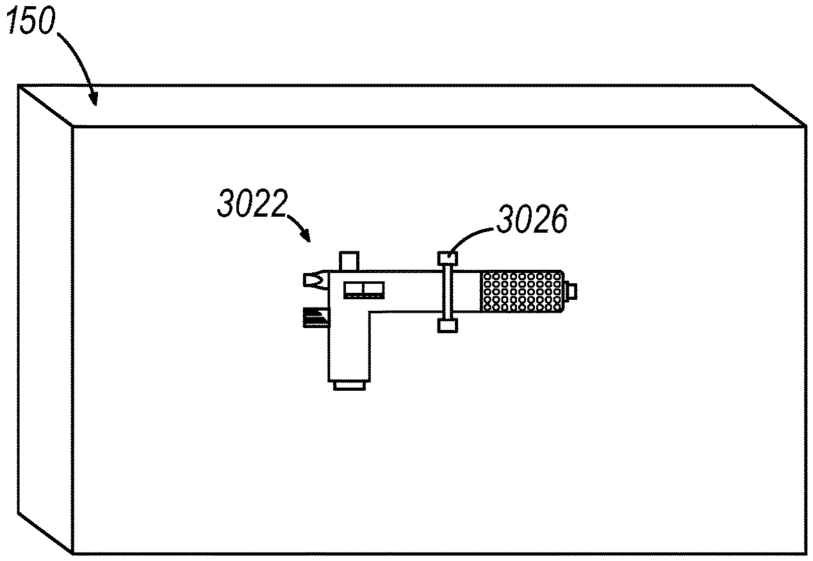
FIG. 7 depicts a side schematic view of the generator of FIG. 5 and the instrument tool assembly of FIG. 6.

Rather than inclusion of tool (3022) in kit (3000), FIG. 7 shows an alternative example with tool (3022) provided or attached to generator (150) associated with instrument (152) (see FIG. 6). In one example, generator (150) includes a mount (3026) for tool (3022) on generator (150), such as on a sidewall of generator (150). Mount (3026) of the present example is configured to support multiple attachments and detachments of tool (3022). Mount (3026) may also include instructions for using tool (3022), a tool part number of tool (3022), a handpiece part number that tool (3022) is associated with, and/or a website where operators may refer for use of generator (150) and tool (3022). Tool (3022), more particularly, also includes electronics (3045) (see FIG. 8) and labels operable to communicate with nearby instrument (152) (see FIG. 6) and/or generator (150). Electronics (3045) includes a central processing unit (CPU), a memory, a communication unit such as a wireless receiver and transmitter, and/or a feedback system such as a haptic button or display. Electronics (3045) are operable with generator (150) and instrument (152) to communicate usage and function data either wired or wirelessly.

Figure 8:
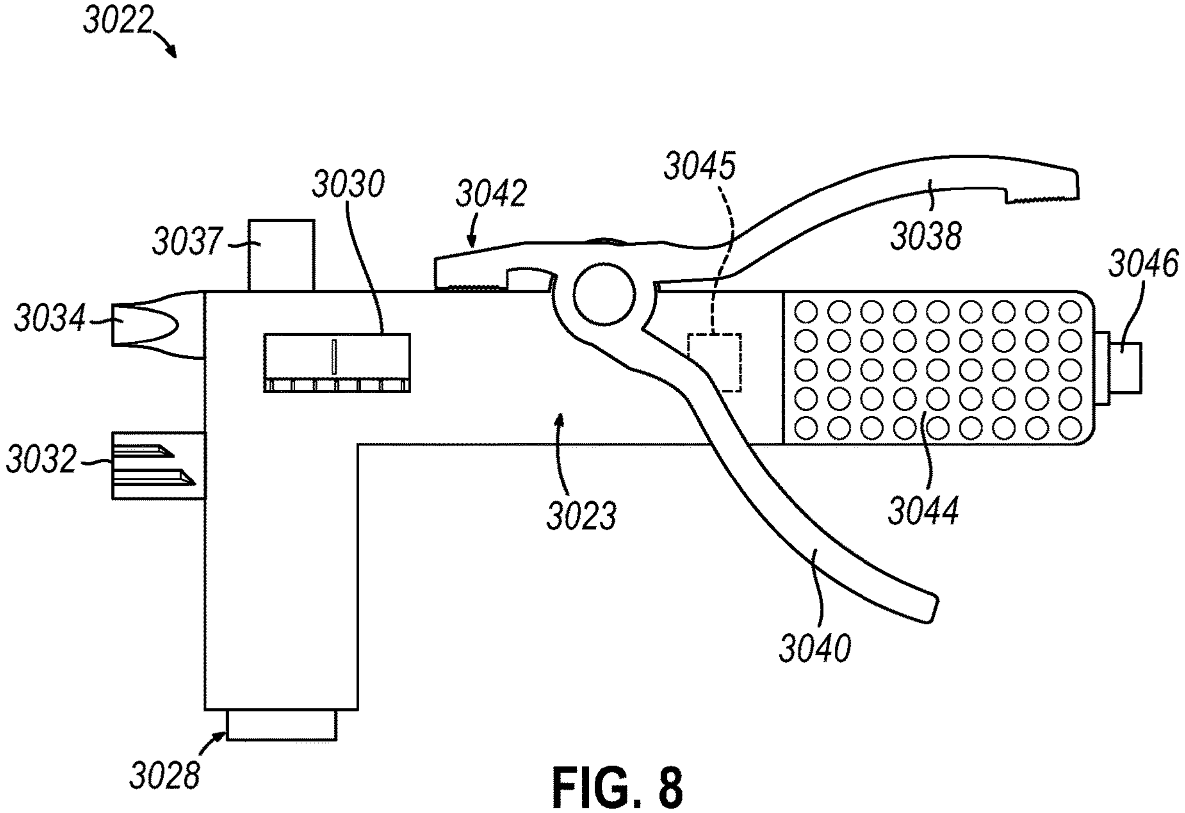
FIG. 8 depicts a front schematic view of the instrument tool assembly of FIG. 6.

FIG. 8 shows one example of tool (3022) in greater detail for assembling or disassembling instrument (152) (see FIG. 6). Tool (3022) may include a body (3023), a torque limiting aspect, such as a torque wrench coupler (3028), affixed to body (3023). Coupler (3028) may fit a traditional hexagonal head faster, a flat-head, Philips-head screw, or any other proprietary or non-proprietary fittings. In one example, tool (3022) includes a predefined torque limit associated with coupler (3028) that is set and calibrated when tool (3022) is produced and is not adjustable by the user. In another example, tool (3022) includes an adjustable torque limit associated with coupler (3028) such that a user is able to set a torque limit from a plurality of available torque limits to change the torque applied as desired by the user. A torque limit indicator (3030) is presented on body (3023) of the present example to indicate the torque limit that the tool (3022) has been adjusted. Adjusting the torque limit may be performed by twisting handle (3044) to an indicated torque limit, such as a click-type torque wrench, by twisting a rotation shaft, such as a T-Handle torque wrench, by pressing a button, such as an electronic torque wrench, or by manipulating some portion of tool (3022) according to a predetermined amount. Upon use, tool (3022) indicates that a desired torque has been reached with an audible noise, a tactile indication, and/or a visual indication. Tool (3022) is also be capable of indicating a current torque being applied without limiting the torque, such as a beam style torque wrench. Torque limiting aspect, such as that associated with coupler (3028), may be selectable to either allow torque limiting or to disable torque limiting, thereby using tool (3022) as a wrench or a ratchet. All torque limiting and torque indicating features may be used in clockwise and/or counter-clockwise rotation and may be presented electronically and/or mechanically.

Tool (3022) further includes a pry portion (3034), which is more particularly shown as a wedge (3034) in the present example, intended to separate and pry apart two components of instrument (152) by wedging pry portion (3034) at a predetermined access portion (3035) between the two components, such as two portions of housing. Separation of the two components at predetermined access portion (3035) may be achieved by either using pry portion (3034) as a lever once it has been wedged between the two components or may also be completed by wedging pry portion (3034) deeper between two components and thus forcing them apart. Pry portion (3034) may be located anywhere on tool (3022) capable of manipulating tool (3022) adequately to achieve the desired separation of the two components. Pry portion (3034) may be used to separate components that have been coupled together, such as with a clip or press pin, adhesive, magnets, fracture areas, or by any other securement. Pry portion (3034) also functions as a scraper to remove biological material or adhesive on the instrument (152) or generator (150).

Tool (3022) of the present example also include a key (3032) intended to unlock portions of instrument (152) and/or the generator (150). Key (3032) may be device specific or generic as to apply to several devices. Key (3032) may be operable to disassemble instrument (152) for component harvesting or may be operable to unlock or access features of instrument (152) that would not otherwise be available. By way of example, key is configured to be received within a lock assembly (not shown) of a hatch (3033) configured to transition from a locked state to an unlocked state. In the locked state, hatch (3033) is secured to inhibit access therethrough to an interior (3036) of instrument (152). In the unlocked state, hatch (3033) is configured to selectively move to allow access to interior (3036) and to remove and/or replace components such as an ultrasonic transducer from the interior (3036).

Tool (3022) of the present example also includes a cleaning tube (3037) configured to scrub and clean instrument (152). More particularly, tool (3022) has a lumen cleaner configured to clean a lumen (not shown) on instrument (152). Cleaning tube (3037) and lumen cleaner may include bristles and contact surfaces configured to clean surfaces.

By way of further example, tool (3022) has a plier (3040) and a spreader (3038). Plier (3040) and spreader (3038) may be separate components or may be included as one component hinged against body (3023) of tool (3022). Plier (3040) and spreader (3038) have handles configured to respectively pinch and spread an arm (3042) against body of tool (3022), as shown in the present example. Plier (3040) and spreader (3038) may also feature a single handle with multiple arms (not pictured), one arm being configured to pinch against body (3023) of tool (3022) and the other arm being configured to spread against body (3023) of tool (3022). Plier (3040) is configured to compress components together, such as assembling multiple components of instrument (152) or may be used to crush components of instrument (152), thereby gaining access to portions of instrument (152). In contrast, spreader (3038) is configured to separate components of instrument (152) and thereby gain access to portions of instrument (152), such as through predetermined access portion (3035).

In one example, tool (3022) may be incorporated into a robotic surgical system. In addition to the following teachings, tool (3022) may be constructed and operable in accordance with at least some of the teachings of U.S. Pat. No. 9,125,662, the disclosure of which is incorporated by reference herein, in its entirety; and/or various other references cited herein. By way of further example, tool (3022) is configured to couple at a robotic coupling (3046) with a complementary component of a robotic arm (123) (see FIG. 2). While tool (3022) is coupled to robotic arm (123), robotic arm (123) can use tool (3022) to disassembly, assembly, and/or clean instrument (152) and generator (152). Robotic arm (123) can use tool (123) on instrument (152) while instrument (152) is in tray (3016), is mounted on generator (150), is freely movable, such as on a table, or is coupled to a complementary robotic arm (123). Robotic arm (123) can use all of the previously mentioned functions of tool (3022) such as changing the torque limit and using torque limiting aspect, using key (3032), using pry portion (3034), and using plier (3040) and spreader (3038). When robotic arm (123) is in proximity to tool (3022), robotic arm (123) can communicate with electronics (3045) to learn how tool (3022) has previously been used and to disable tool (3022) from future use. Communication between robotic arm (123) and tool (3022) can be completed wirelessly or through a wired link at robotic coupling (3046).

As noted above, tool (3022) in one example includes electrical features and/or electrically conductive mechanical features. Such features may provide a risk of power or signals undesirably crossing from one electrical feature to another electrical feature and/or from one electrical feature to an electrically conductive mechanical feature. In addition, tool (3022) may include electrical features and/or electrically conductive mechanical features that may provide a risk of generating electrical potentials between proximate components or creating capacitive couplings between electrical features and/or between an electrical feature and an electrically conductive mechanical feature. In the context of tool (3022), such risks may occur with respect to the components that tool (3022) are coupled with. Other components of tool (3022) that may present the above-described risks will be apparent to those skilled in the art in view of the teachings herein.

Figure 9A:
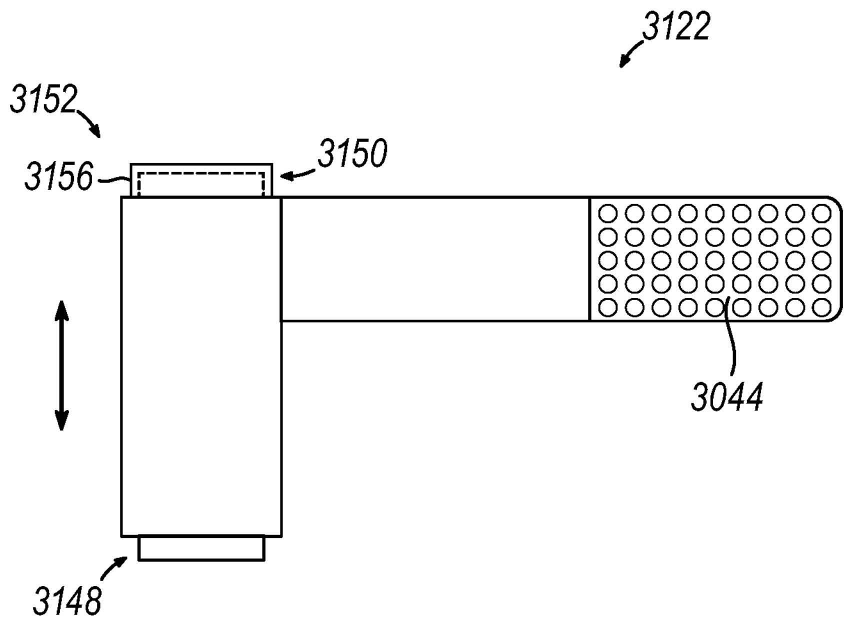
FIG. 9A depicts a front schematic view of another example of an instrument tool assembly in a first configuration.
Figure 9B:
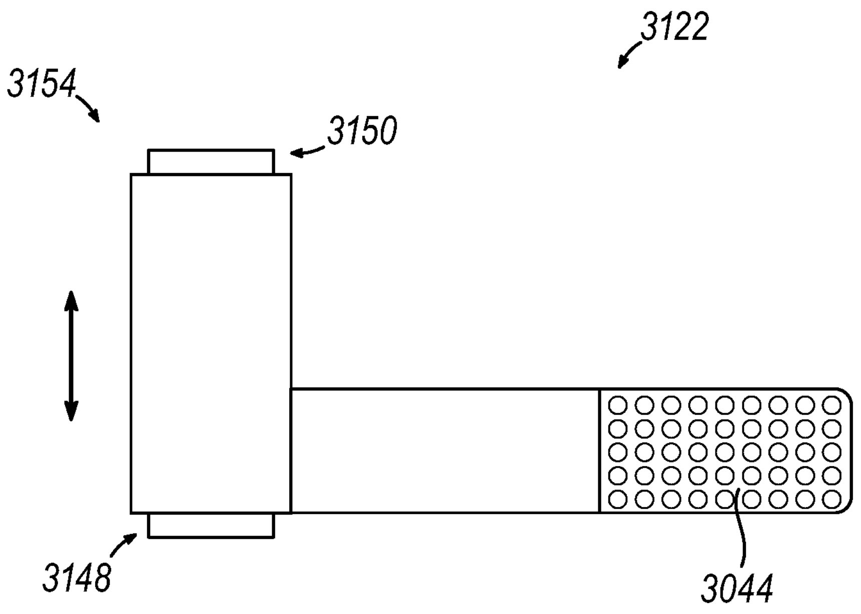
FIG. 9B depicts a front schematic view of the instrument tool assembly of FIG. 9A in a second configuration.

Referring to FIGS. 9A and 9B shows another example of a tool (3122) similar to tool (3022) (see FIG. 8) except as otherwise discussed below. FIG. 9A shows tool (3122) in a first configuration (3152) such that tool (3122) may be used in a particular manner with a first feature (3048) enabled. First feature (3148) may include any of the above features of tool (3022) (see FIG. 8) described above, such as torque wrench coupler (3028), key (3032), pry portion (3034), cleaning tube (3037), spreader (3038), plier (3040), handle (3044), linking with electronics (3045), and robotic coupling (3046) (see FIG. 8). Tool (3122) is configured such that once first feature (3148) is utilized for its intended purpose, a second feature (3150) of tool (3122) becomes operable after use of first feature (3148), and in one example, only after use of first feature (3148). Again, second feature (3150) may include any of the above features of tool (3022) described above, such as torque wrench coupler (3028), key (3032), pry portion (3034), cleaning tube (3037), spreader (3038), plier (3040), handle (3044), linking with electronics (3045), and robotic coupling (3046) (see FIG. 8). While any combination of features of tool (3022) (see FIG. 8) may be incorporated into tool (3122), in the present example, first feature (3148) includes torque wrench coupler (3028) and second feature (3150) includes pry portion (3034), although the invention is not intended to be unnecessarily limited to this particular combination of present example. In the present example, the tool (3122) can be automatically transitioned from first feature (3148) to second feature (3150) once torque wrench coupler (3028) has reached a predefined torque. Transitioning tool (3122) from first feature (3148) to second feature (3150) can change the way a user holds and operates tool (3122).

To enable second feature (3150), tool (3122) transitions from first configuration (3152) to a second configuration (3154) as shown in FIG. 9B. Tool (3122) also includes a feature inhibitor (3156), such as a cap. To this end, when in first configuration (3152), feature inhibitor (3156) is configured to inhibit access to and/or function of second feature (3150) prior to use of first feature (3148). Feature inhibitor (3156) may further include a warning indicia thereon, such as an instruction that first feature (3148) is to be used or that tool (3122) is to be transitioned to the second configuration (3154) prior to second feature (3150) becoming accessible and/or used. Tool (3122) may require removal or destruction of feature inhibitor (3156) to make second feature (3150) operable or accessible. When in the second configuration (3154), tool (3022) is configured to disable first feature (3148) such that first feature (3148) is no longer accessible and/or operable. For example, feature inhibitor (3156) as cap may be placed to cover and/or hide first feature (3148) so that first feature (3148) is no longer accessible and/or visible. Tool (3122) in one example is required to be reset to further make operable first feature (3148) by resetting tool (3122) to first configuration (3152). In one example, when in the second configuration (3154), both the first feature (3048) and second feature (3050) of tool (3022) operable. In this respect, the invention is not intended to be unnecessarily limited to successive operation and access of first and second features (3148, 3150) as shown in the present example.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical kit, comprising: (a) a surgical instrument, including: (i) an end effector, (ii) a shaft assembly configured to proximally extend from the end effector, and (iii) a body assembly configured to proximally extend from the shaft assembly; wherein at least one of the end effector, the shaft assembly, or the end effector has a predetermined access portion configured to be at least partially removed therefrom for accessing an interior therein; and (b) an instrument tool assembly, including: (i) a tool body, (ii) a torque wrench operatively connected to the tool body, and (iii) a removal portion operatively connected to the tool body and configured to selectively engage the predetermined access portion of the surgical instrument and thereby at least partially remove the predetermined access portion for accessing the interior of the surgical instrument.

Example 2

The surgical kit of Example 1, wherein the body assembly includes a body housing, and wherein the body housing includes the interior and the predetermined access portion for at least partially removing the predetermined access portion of the body housing from a remainder of the body housing, wherein the body housing with the predetermined access portion removed therefrom defines a body opening.

Example 3

The surgical kit of Example 2, wherein the body assembly further includes an internal component within the interior and configured to be removed through the opening.

Example 4

The surgical kit of Example 3, wherein the internal component includes an ultrasonic transducer.

Example 5

The surgical kit of Example 1, wherein the removal portion includes a lever configured to pry the predetermined access portion from the remainder of the surgical instrument.

Example 6

The surgical kit of Example 1, wherein the predetermined access portion includes a hatch configured to transition from a locked state to an unlocked state, wherein the hatch in the locked state is secured to inhibit access therethrough to the interior, and wherein the hatch in the unlocked state is configured to selectively move to allow access to the interior.

Example 7

The surgical kit of Example 6, wherein the instrument tool assembly includes a key configured to selectively direct the hatch from the locked state to the unlocked state.

Example 8

The surgical kit of Example 1, wherein the torque wrench has a restricted state and an unrestricted state, wherein the torque wrench in the restricted state is configured to limit torque applied thereby, and wherein the torque wrench in the unrestricted state is configured to not limit torque applied thereby.

Example 9

The surgical kit of Example 1, further comprising a bag configured to receive and fluidly seal a portion of the surgical instrument therein for storage after use.

Example 10

The surgical kit of Example 1, wherein the instrument tool assembly further includes a robotic interface configured to connect to a robot for robotic disassembly of the surgical instrument.

Example 11

The surgical kit of Example 1, wherein the removal portion includes: (i) a removal tool operatively connected to the tool body and configured to selectively engage the predetermined access portion of the surgical instrument, and (ii) a tool shield configured to cover at least a portion of the removal tool thereby rendering the removal tool unusable, wherein the tool shield is further configured to be selectively moved relative to the removal tool thereby uncovering the at least the portion of the removal tool and rendering the removal tool usable.

Example 12

The surgical kit of Example 1, further comprising a packaging, including: (i) a support body configured to receive at least one of the surgical instrument or the instrument tool for storage, and (ii) a removal tool singularly and unitarily formed with the support body, wherein the removal tool is configured to selectively engage the predetermined access portion of the surgical instrument and thereby at least partially remove the predetermined access portion for accessing the interior of the surgical instrument.

Example 13

The surgical kit of Example 1, wherein the removal portion includes a removal tool operatively connected to the tool body and configured to selectively engage the predetermined access portion of the surgical instrument, wherein the removal tool is configured to be unusable until the torque wrench has been used.

Example 14

The surgical kit of Example 13, wherein the torque wrench is configured to be unusable once the torque wrench has been used.

Example 15

The surgical kit of Example 1, wherein the instrument tool includes a communication unit configured to communicate with at least one of the surgical instrument or a generator for indicating use to an operator.

Example 16

A surgical system, comprising: (a) an instrument tool assembly, including: (i) a tool body, (ii) a torque wrench operatively connected to the tool body and having a torque portion configured to transition from a first state to a second state, and (iii) a removal portion having a removal tool operatively connected to the tool body and configured to selectively engage a predetermined access portion of a surgical instrument and thereby at least partially remove the predetermined access portion for accessing an interior of the surgical instrument, wherein the removal tool is configured to be unusable until the torque portion transitions from the first state to the second state.

Example 17

The surgical system of Example 16, further comprising a surgical device having a tool mount, wherein the instrument tool is configured to be releasably secured to the tool mount.

Example 18

The surgical system of Example 16, further comprising a packaging, including: (i) a support body configured to receive at least one of the surgical instrument or the instrument tool for storage, and (ii) a removal tool singularly and unitarily formed with the support body, wherein the removal tool is configured to selectively engage the predetermined access portion of the surgical instrument and thereby at least partially remove the predetermined access portion for accessing the interior of the surgical instrument.

Example 19

The surgical system of Example 18, further comprising a bag configured to receive and fluidly seal a portion of a surgical instrument therein for storage after use.

Example 20

A method of accessing an interior of a surgical instrument with an instrument tool, the instrument tool including (i) a tool body, (ii) a torque wrench operatively connected to the tool body, and (iii) a removal portion operatively connected to the tool body, the method comprising: (a) selectively engaging a predetermined access portion of the surgical instrument and thereby at least partially removing the predetermined access portion to access the interior of the surgical instrument.

IV. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/854,065, entitled "Method of Reclaiming Portions of Surgical Instruments for Remanufacturing and Sustainability," filed on Jun. 30, 2022 even date herewith, published as U.S. Pub. No. 2024/0006048 on Jan. 4, 2024, now abandoned, the disclosure of which is incorporated, by reference herein. Various suitable ways in which the teachings herein may be combined with the teachings of U.S. patent application Ser. No. 17/854,065 will be apparent to those of ordinary skill in the art in view of the teachings herein.

In addition to the foregoing, the teachings herein may be readily combined with the teachings of U.S. patent application Ser. No. 17/854,050, entitled "Surgical Instrument with Predetermined Separation Features for Waste Stream Utilization and Related Methods," filed on Jun. 30, 2022, published as U.S. Pub. No. 2024/0000474 on Jan. 4, 2024, the disclosure of which is incorporated by reference herein. Various suitable ways in which the teachings herein may be combined with the teachings of U.S. patent application Ser. No. 17/854,050 will be apparent to those of ordinary skill in the art in view of the teachings herein.

In addition to the foregoing, the teachings herein may be readily combined with the teachings of U.S. patent application Ser. No. 17/854,166, entitled "Surgical Instrument with Removable Cable and Associated Couplings," filed on Jun. 30, 2022, published as U.S. Pub. No. 2024/0006810 on Jan. 4, 2024, the disclosure of which is incorporated by reference herein. Various suitable ways in which the teachings herein may be combined with the teachings of U.S. patent application Ser. No. 17/854,166 will be apparent to those of ordinary skill in the art in view of the teachings herein.

In addition to the foregoing, the teachings herein may be readily combined with the teachings of U.S. patent application Ser. No. 17/854,104, entitled "Robotic Surgical System with Removable Portion and Method of Disassembling Same," filed on Jun. 30, 2022, published as U.S. Pub. No. 2024/0000526 on Jan. 1, 2024, the disclosure of which is incorporated by reference herein. Various suitable ways in which the teachings herein may be combined with the teachings of U.S. patent application Ser. No. 17/854,104 will be apparent to those of ordinary skill in the art in view of the teachings herein.

In addition to the foregoing, the teachings herein may be readily combined with the teachings of U.S. patent application Ser. No. 17/854,110, entitled "System for Determining Disposal of Surgical Instrument and Related Methods," filed on Jun. 30, 2022, published as U.S. Pub. No. 2024/0001416 on Jan. 1, 2024, the disclosure of which is incorporated by reference herein. Various suitable ways in which the teachings herein may be combined with the teachings of U.S. patent application Ser. No. 17/854,110 will be apparent to those of ordinary skill in the art in view of the teachings herein.

In addition to the foregoing, the teachings herein may be readily combined with the teachings of U.S. patent application Ser. No. 17/854,114, entitled "Reclamation Packaging for Surgical Instrument and Related Methods," filed on Jun. 30, 2022, published as U.S. Pub. No. 2024/0000491 on Jan. 1, 2024, the disclosure of which is incorporated by reference herein. Various suitable ways in which the teachings herein may be combined with the teachings of U.S. patent application Ser. No. 17/854,114 will be apparent to those of ordinary skill in the art in view of the teachings herein.

In addition to the foregoing, the teachings herein may be readily combined with the teachings of U.S. patent application Ser. No. 17/854,120, entitled "Surgical Instrument with Various Alignment Features and Methods for Improved Disassembly and Assembly," filed on Jun. 30, 2022, published as U.S. Pub. No. 2024/0000475 on Jan. 1, 2024, the disclosure of which is incorporated by reference herein. Various suitable ways in which the teachings herein may be combined with the teachings of U.S. patent application Ser. No. 17/854,120 will be apparent to those of ordinary skill in the art in view of the teachings herein.

In addition to the foregoing, the teachings herein may be readily combined with the teachings of U.S. patent application Ser. No. 17/854,127, entitled "Surgical System and Methods for Instrument Assessment and Cleaning," filed on Jun. 30, 2022, published as U.S. Pub. No. 2024/0003820 on Jan. 1, 2024, the disclosure of which is incorporated by reference herein. Various suitable ways in which the teachings herein may be combined with the teachings of U.S. patent application Ser. No. 17/854,127 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK® bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical kit, comprising:

(a) a surgical instrument, including:

(i) an end effector, (ii) a shaft assembly configured to proximally extend from the end effector, and (iii) a body assembly configured to proximally extend from the shaft assembly, wherein at least one of the end effector, the shaft assembly, or the body assembly has a predetermined access portion configured to be at least partially removed therefrom for accessing an interior of the surgical instrument; and (b) an instrument tool assembly, including:

(i) a tool body, (ii) a torque wrench operatively connected to the tool body, wherein the torque wrench is configured to adjustably select a torque limit, and (iii) a removal portion operatively connected to the tool body and configured to selectively engage the predetermined access portion of the surgical instrument and thereby at least partially remove the predetermined access portion for accessing the interior of the surgical instrument, wherein the removal portion includes a removal tool operatively connected to the tool body and configured to selectively engage the predetermined access portion of the surgical instrument, wherein the removal tool is configured to be unusable until the torque wrench has been used.

2. The surgical kit of claim 1, wherein the body assembly includes a body housing, and wherein the body housing includes the interior and the predetermined access portion for at least partially removing the predetermined access portion of the body housing from a remainder of the body housing, wherein the body housing with the predetermined access portion removed therefrom defines a body opening.

3. The surgical kit of claim 2, wherein the body assembly further includes an internal component within the interior and configured to be removed through the body opening.

4. The surgical kit of claim 3, wherein the internal component includes an ultrasonic transducer.

5. The surgical kit of claim 1, wherein the removal portion includes a lever configured to pry the predetermined access portion from a remainder of the surgical instrument.

6. The surgical kit of claim 1, wherein the predetermined access portion includes a hatch configured to transition from a locked state to an unlocked state, wherein the hatch in the locked state is secured to inhibit access therethrough to the interior, and wherein the hatch in the unlocked state is configured to selectively move to allow access to the interior.

7. The surgical kit of claim 6, wherein the instrument tool assembly includes a key configured to selectively direct the hatch from the locked state to the unlocked state.

8. The surgical kit of claim 1, wherein the torque wrench has a restricted state and an unrestricted state, wherein the torque wrench in the restricted state is configured to limit torque applied thereby, and wherein the torque wrench in the unrestricted state is configured to not limit torque applied thereby.

9. The surgical kit of claim 1, further comprising a bag configured to receive and fluidly seal a portion of the surgical instrument therein for storage after use.

10. The surgical kit of claim 1, wherein the instrument tool assembly further includes a robotic interface configured to connect to a robot for robotic disassembly of the surgical instrument.

11. The surgical kit of claim 1, wherein the removal portion includes:

a tool shield configured to cover at least a portion of the removal tool thereby rendering the removal tool unusable, wherein the tool shield is further configured to be selectively moved relative to the removal tool thereby uncovering the at least the portion of the removal tool and rendering the removal tool usable.

12. The surgical kit of claim 1, further comprising a packaging, including a support body configured to receive at least one of the surgical instrument or the instrument tool assembly for storage.

13. The surgical kit of claim 1, wherein the torque wrench is configured to be unusable once the torque wrench has been used.

14. The surgical kit of claim 1, wherein the instrument tool assembly includes electronics configured to communicate with at least one of the surgical instrument or a generator for indicating use to an operator.

15. A surgical kit, comprising:

(a) a surgical instrument, including:

(i) an end effector, (ii) a shaft assembly configured to proximally extend from the end effector, and (iii) a body assembly configured to proximally extend from the shaft assembly, wherein at least one of the end effector, the shaft assembly, or the body assembly has a predetermined access portion configured to be at least partially removed therefrom for accessing an interior of the surgical instrument; and (b) an instrument tool assembly, including:

(i) a tool body, (ii) a torque wrench operatively connected to the tool body, and (iii) a removal portion operatively connected to the tool body and configured to selectively engage the predetermined access portion of the surgical instrument and thereby at least partially remove the predetermined access portion for accessing the interior of the surgical instrument, wherein the removal portion includes a removal tool operatively connected to the tool body and configured to selectively engage the predetermined access portion of the surgical instrument, wherein the removal tool is configured to be unusable until the torque wrench has been used.

16. The surgical kit of claim 15, wherein the body assembly includes a body housing, and wherein the body housing includes the interior and the predetermined access portion for at least partially removing the predetermined access portion of the body housing from a remainder of the body housing, wherein the body housing with the predetermined access portion removed therefrom defines a body opening.

17. The surgical kit of claim 16, wherein the body assembly further includes an internal component within the interior and configured to be removed through the body opening.

18. The surgical kit of claim 15, wherein the predetermined access portion includes a hatch configured to transition from a locked state to an unlocked state, wherein the hatch in the locked state is secured to inhibit access therethrough to the interior, and wherein the hatch in the unlocked state is configured to selectively move to allow access to the interior.

19. A surgical kit, comprising:

(a) a surgical instrument, including:

(i) an end effector, (ii) a shaft assembly configured to proximally extend from the end effector, and (iii) a body assembly configured to proximally extend from the shaft assembly, wherein at least one of the end effector, the shaft assembly, or the body assembly has a predetermined access portion configured to be at least partially removed therefrom for accessing an interior of the surgical instrument; and (b) an instrument tool assembly, including:

(i) a tool body, (ii) a torque wrench operatively connected to the tool body, and (iii) a removal portion operatively connected to the tool body and configured to selectively engage the predetermined access portion of the surgical instrument and thereby at least partially remove the predetermined access portion for accessing the interior of the surgical instrument, wherein the torque wrench is configured to be unusable once the torque wrench has been used.

* * * * *